United States Patent [19]

Eicken et al.

[11] 4,295,875
[45] Oct. 20, 1981

[54] TETRAHYDRO-1,3-OXAZINES

[75] Inventors: Karl Eicken, Wachenheim; Wolfgang Rohr, Mannheim; Hans J. Pander, Roedersheim-Gronau; Bruno Wuerzer, Limburgerhof, all of Fed. Rep. of Germany

[73] Assignee: BASF Aktiengesellschaft, Fed. Rep. of Germany

[21] Appl. No.: 132,986

[22] Filed: Mar. 24, 1980

Related U.S. Application Data

[63] Continuation of Ser. No. 57,129, Jul. 12, 1979, abandoned.

[30] Foreign Application Priority Data

Jul. 27, 1978 [DE] Fed. Rep. of Germany ....... 2832890

[51] Int. Cl.$^3$ .................. A01N 43/86; C07D 265/04; C07D 265/12
[52] U.S. Cl. ............................................. 71/88; 71/92; 544/6; 544/88; 544/92
[58] Field of Search ....................... 544/88, 90; 71/88

[56] References Cited

U.S. PATENT DOCUMENTS 3,719,466 3/1973 Ahle ........................................ 71/88
3,989,503 11/1976 Pallos et al. ............................. 71/88
4,021,224 5/1977 Pallos et al. ............................. 71/88

FOREIGN PATENT DOCUMENTS 2402983 8/1974 Fed. Rep. of Germany .......... 71/88
2620101 11/1976 Fed. Rep. of Germany ........ 544/88

Primary Examiner—John D. Randolph
Attorney, Agent, or Firm—Keil & Witherspoon

[57] ABSTRACT

New tetrahydro-1,3-oxazines of the formula

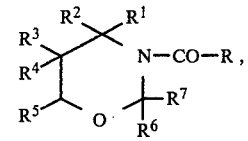

where R denotes linear or branched haloalkyl of up to 3 carbon atoms, $R^1$, $R^2$, $R^3$, $R^4$ and $R^5$ are identical or different and each denotes hydrogen or linear or branched alkyl of up to 3 carbon atoms, $R^6$ denotes hydrogen or linear or branched alkyl of up to 8 carbon atoms, $R^7$ denotes hyrogen, linear or branched alkyl of up to 8 carbon atoms, alkoxyalkyl of up to 6 carbon atoms or dialkoxyalkyl of up to 8 carbon atoms, and $R^6$ and $R^7$ may together form a methylene chain of 4 or 5 carbon atoms.

The compounds are antagonistic agents and, as such, increase the tolerance of herbicidal acetanilides by crop plants. Herbicidal agents containing the tetrahydro-1,3-oxazines in combination with haloacetanilides are suitable for combating unwanted plant growth in Indian corn and cereal crops.

10 Claims, No Drawings

TETRAHYDRO-1,3-OXAZINES

This is a continuation, of application Ser. No. 57,129, filed July 12, 1979 now abandoned.

The present invention relates to new tetrahydro-1,3-oxazines, herbicidal agents containing, as herbicidal active ingredients, substituted acetanilides and, as antagonistic agents, these tetrahydro-1,3-oxazines, and a process for selectively combating unwanted plant growth with these herbicidal agents.

Substituted acetanilides of the formula

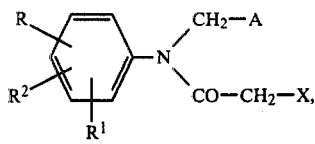

where R denotes hydrogen, linear or branched alkyl or alkoxy of up to 5 carbon atoms, $R^1$ denotes hydrogen, halogen, or linear or branched alkyl or alkoxy of up to 5 carbon atoms, $R^2$ denotes hydrogen, halogen, or linear or branched alkyl or alkoxy of up to 5 carbon atoms, R together with $R^2$ denotes an alkylene chain of up to 6 carbon atoms which is linked in the o-position and may be substituted by linear or branched alkyl of up to 4 carbon atoms, X denotes chlorine or bromine, and A denotes azole which is attached via a ring nitrogen atom and may be mono- or polysubstituted by halogen, phenyl, alkyl, alkoxy, alkylthio or perfluoroalkyl, each of up to 4 carbon atoms, cyano, carboxy, carbalkoxy of up to 4 carbon atoms in the alkoxy, or alkanoyl of up to 4 carbon atoms, or A denotes salts of azoles containing 2 or 3 nitrogen atoms, have an excellent herbicidal action, but cause damage to crops such as Indian corn and Gramineae.

It was therefore the object of the invention to provide antagonistic agents which offset this poor tolerance of herbicidal acetanilides by certain crop plants.

Herbicidal agents containing, in addition to chloroacetanilides as herbicidal active ingredients, antagonistic compounds have been disclosed in U.S. Pat. No. 3,719,466 and German Laid-Open Applications DE-OS 2,218,097 and 2,402,983. U.S. Pat. No. 3,719,466 teaches that damage to sorghum and wheat caused by the herbicide 2-chloro-2',6'-diethyl-N-(methoxymethyl)-acetanilide can be avoided by treating the seed with an antagonistic agent such as N,N-diallylacetamide.

German Laid-Open Application DE-OS No. 2,218,097 mentions combinations of the same active ingredient and other herbicidal acetanilides with antagonistic amides, e.g., N,N-diallyldichloroacetamide. However, these amides are preferably used as antidotes for herbicidal thiolcarbamates.

German Laid-Open Application DE-OS No. 2,402,983 relates to herbicidal agents containing dichloroacetamides known from German Laid-Open Application DE-OS No. 2,218,097, or dichloroacetamides structurally similar to them, and chloroacetanilides of a different constitution, especially N-(2'-methoxyethyl)-2,6-dimethylchloroacetanilide. These agents are suitable merely for selective weed control in Indian corn. Also said to be suitable as antagonistic compounds are, inter alia, dichloroacetamides in which both substituents on the nitrogen atom form, with it, a 6-membered heterocycle containing a further hetero atom and which is unsubstituted or mono- or polysubstituted by lower alkyl. However, the only representative of this group which is mentioned is N-dichloroacetylmorpholine.

We have found that new tetrahydro-1,3-oxazines of the formula

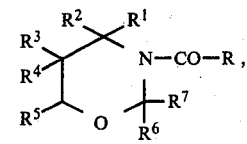

where R denotes linear or branched haloalkyl of up to 3 carbon atoms, $R^1$, $R^2$, $R^3$, $R^4$ and $R^5$ are identical or different and each denotes hydrogen or linear or branched alkyl of up to 3 carbon atoms, $R^6$ denotes hydrogen or linear or branched alkyl of up to 8 carbon atoms, $R^7$ denotes hydrogen, linear or branched alkyl of up to 8 carbon atoms, alkoxyalkyl of up to 6 carbon atoms or dialkoxyalkyl of up to 8 carbon atoms, and $R^6$ and $R^7$ may together form a methylene chain of 4 or 5 carbon atoms, are excellently suited for increasing the tolerance of crop plants to herbicidal substituted acetanilides of the formula I. Herbicidal agents containing at least one substituted acetanilide of the formula I and at least one tetrahydro-1,3-oxazine of the formula II may be used both in Indian corn and in cereal crops. The good herbicidal action of the acetanilides is retained and damage to the crop plants is prevented.

Acetanilides whose tolerance by crop plants can be increased by the new tetrahydro-1,3-oxazines are those of the formula I in which R is hydrogen, alkyl of a maximum of 5 carbon atoms, such as methyl, ethyl, n-propyl, isopropyl, n-butyl, sec-butyl, isobutyl, tert-butyl, linear and branched pentyl, and alkoxy of a maximum of 5 carbon atoms, such as methoxy, ethoxy, propoxy, butoxy and pentoxy;

$R^1$ and $R^2$ are hydrogen, halogen, such as fluorine, chlorine, bromine and iodine, alkyl of a maximum of 5 carbon atoms, such as methyl, ethyl, p-propyl, isopropyl, p-butyl, sec-butyl, isobutyl, tert-butyl, linear and branched pentyl, and alkoxy of a maximum of 5 carbon atoms, such as methoxy, ethoxy, propoxy, butoxy, and pentoxy;

$R^2$ together with R is an alkylene chain of a maximum of 6 carbon atoms, linked in the o-position and unsubstituted or substituted by alkyl of a maximum of 4 carbon atoms, e.g., ethylene, trimethylene, tetramethylene, 1-methyltrimethylene, 1,1-dimethyltrimethylene, and 1,1-dimethyltetramethylene;

X is chlorine, bromine or iodine, preferably chlorine;

A is an azole attached via a ring nitrogen atom, e.g., pyrrole, pyrazole, imidazole, 1,2,4-triazole, 1,2,3-triazole, and tetrazole, which be mono- or polysubstituted by halogen, phenyl, alkyl, alkoxy, alkylthio or perfluoroalkyl, each of up to 4 carbon atoms, cyano, carboxy, or carbalkoxy with up to 4 carbon atoms in the alkoxy, or alkanoyl of up to 4 carbon atoms, the substituents being identical or different, such as 2,6-dimethylpyrrole, tetramethylpyrrole, 3(5)-methylpyrazole, 4-methylpyrazole, 3(5)-ethylpyrazole, 4-ethylpyrazole, 3(5)-isopropylpyrazole, 4-isopropylpyrazole, 3,5-dimethylpyrazole, 3,5-dimethyl-4-acetylpyrazole, 3,5-dimethyl-4-propionylpyrazole, 3,4,5-trimethylpyrazole, 3(5)-phenylpyrazole, 4-phenylpyrazole, 3,5-diphenylpyrazole, 3(5)-phenyl-5(3)-methylpyrazole, 3(5)- chloropyrazole, 4-chloropyrazole, 4-bromopyrazole, 4-iodopyrazole, 3,4,5-tribromopyrazole, 3,5-dimethyl-4-chloropyrazole, 3,5-dimethyl-4-bromopyrazole, 4-chloro-3(5)-methylpyrazole, 4-bromo-3(5)-methylpyrazole, 4-methyl-3,5-dichloropyrazole, 3(5)-methyl-4,5(3)-dichloropyrazole, 3(5)-chloro-5(3)-methylpyrazole, 4-methoxypyrazole, 3(5)-methyl-5(3)-methoxypyrazole, 3(5)-ethoxy-4,5(3)-dimethylpyrazole, 3(5)-methyl-5(3)-trifluoromethylpyrazole, 3,5-bis-trifluoromethylpyrazole, 3(5)-methyl-5(3)-carbethoxypyrazole, 3,5-bis-carbethoxypyrazole, 3,4,5-triscarbethoxypyrazole, 3(5)-methyl-5(3)-methylthio-4-carbethoxypyrazole, 4-methyl-3,5-biscarbethoxypyrazole, 4-cyanopyrazole, 4-methoxy-3,5-dichloropyrazole, 4,5-dichloroimidazole, 2-ethyl-4,5-dichloroimidazole, 2-methyl-4,5-dichloroimidazole, 3(5)-methyl-1,2,4-triazole, 3,5-dimethyl-1,2,4-triazole, 3(5)-chloro-1,2,4-triazole, 3(5)-bromo-1,2,4-triazole, 3(5)-chloro-5(3)-methyl-1,2,4-triazole, 3,5-dichloro-1,2,4-triazole, 3,5-dibromo-1,2,4-triazole, 3(5)-chloro-5(3)-cyano-1,2,4-triazole, 3(5)-chloro-5(3)-phenyl-1,2,4-triazole, 3(5)-chloro-5(3)-carbomethoxy-1,2,4-triazole, 3(5)-methylthio-1,2,4-triazole, 4(5)-methyl-1,2,3-triazole, 4,5-dimethyl-1,2,3-triazole, 4(5)-phenyl-1,2,3-triazole, 4(5)-chloro-1,2,3-triazole, 1,2,3-triazol-4(5)-carboxylic acid ethyl ester, 1,2,3-triazol-4,5-yl-dicarboxylic acid dimethyl ester, 5-methyltetrazole, 5-chlorotetrazole, and tetrazolyl-5-carboxylic acid ethyl ester.

Furthermore, the radical A may, when the optionally substituted azole contains 2 or 3 nitrogen atoms, also be attached in a saltlike manner to one of the usual strong inorganic or organic acids, e.g., hydrochloric acid, hydrobromic acid, nitric acid, sulfuric acid, tetrafluoboric acid, fluosulfonic acid, and formic acid, a halogenated carboxylic acid, e.g., trichloroacetic acid, an alkanesulfonic acid, e.g., methanesulfonic acid, a halogenated alkanesulfonic acid, e.g., trifluoromethanesulfonic acid and perfluorohexanesulfonic acid, and an arylsulfonic acid, e.g. dodecylbenzenesulfonic acid.

Preferred acetanilides are those which bear methyl or ethyl in the 2- and 6-positions on the phenyl ring and hydrogen, methyl or ethyl in the 3-position; suitable azoles are pyrazole, imidazole, triazole and tetrazole, which are unsubstituted or substituted by lower alkyl, alkoxy, alkylthio, carbalkoxy, cyano or halogen.

In particular, the herbicidal agents according to the invention contain the following acetanilides:
2-chloro-2',6'-dimethyl-N-(pyrazol-1-yl-methyl)-acetanilide, 2-chloro-2'-methyl-6'-ethyl-N-(pyrazol-1-yl-methyl)-acetanilide, 2-chloro-2',6'-dimethyl-N-(4-methylpyrazol-1-yl-methyl)-acetanilide, 2-chloro-2-methyl-6-ethyl-N-(4-methoxypyrazol-1-yl-methyl)-acetanilide, 2-chloro-2'-methyl-6'-ethyl-N-(3(5)-methyl-pyrazol-1-yl)-acetanilide, 2-chloro-2',6'-dimethyl-N-(3,5-dimethylpyrazol-1-yl-methyl)-acetanilide, 2-chloro-2',6'-dimethyl-N-(1,2,4-triazol-1-yl-methyl)-acetanilide, 2-chloro-2',6'-dimethyl-N-(4-chloropyrazol-1-yl-methyl)-acetanilide, 2-chloro-2',3',6'-trimethyl-N-(pyrazol-1-yl-methyl)-acetanilide, 2-chloro-2'-methyl-6'-ethyl-N-(3,5-dimethylpyrazol-1-yl-methyl)-acetanilide, 2-chloro-2',6'-diethyl-N-(3,5-dimethylpyrazol-1-yl-methyl)-acetanilide, 2-chloro-2',3',6'-trimethyl-N-(3,5-dimethylpyrazol-1-yl-methyl)-acetanilide, 2-chloro-2',6'-diethyl-N-(4-methylpyrazol-1-yl-methyl)-acetanilide, 2-chloro-2'-methyl-6'-ethyl-N-(4-methylpyrazol-1-ylmethyl)-acetanilide, 2-chloro-2',3',6'-trimethyl-N-(4-methylpyrazol-1-yl-methyl)-acetanilide, 2-chloro-2',6'-dimethyl-N-(3-(5)-methylpyrazol-1-yl-methyl)-acetanilide, 2-chloro-2',6'-diethyl-N-(3-(5)-methylpyrazol-1-yl-methyl)-acetanilide, 2-chloro-2',6'-dimethyl-N-(4-methoxypyrazol-1-yl-methyl)-acetanilide, 2-chloro-2',6'-diethyl-N-(pyrazol-1-yl-methyl)-acetanilide, 2-chloro-2',6'-dimethyl-N-(4,5-dichloroimidazol-1-yl-methyl)-acetanilide, 2-chloro-2'-methyl-6'-ethyl-N-(4,5-dichloroimidazol-1-yl-methyl)-acetanilide, 2-chloro-2'-methyl-6'-ethyl-N-(2-ethyl-4,5-dichloroimidazol-1-yl-methyl)-acetanilide, 2-chloro-2',6'-diethyl-N-(4,5-dichloroimidazol-1-yl-methyl)-acetanilide, 2-chloro-2'-methyl-6'-ethyl-N-(1,2,4-triazol-1-yl-methyl)-acetanilide, 2-chloro-2',6'-diethyl-N-(1,2,4-triazol-1-yl-methyl)-acetanilide and 2-chloro-2',3',6'-trimethyl-N-(1,2,4-triazol-1-yl-methyl)-acetanilide.

The acetanilides of the formula I are disclosed in German Laid-Open Application DE-OS No. 2,648,008 and German Patent Application P 27 44 396. They may be obtained by reaction of 2-halo-N-halomethylacetanilides of the formula V with a 1H-azole of the formula H-A in accordance with the following equation:

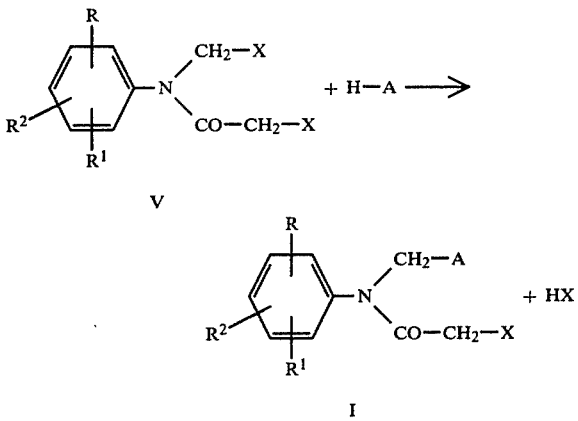

R, $R^1$, $R^2$ and X have the above meanings and A denotes an azole linked via a ring nitrogen atom and which may be mono- or polysubstituted by halogen, phenyl, alkyl, alkoxy, alkylthio or perfluoroalkyl, each of up to 4 carbon atoms, cyano, carboxy, carbalkoxy of up to 4 carbon atoms in the alkoxy or alkanoyl of up to 4 carbon atoms.

Suitable antagonistic agents are tetrahydro-1,3-oxazines of the formula II in which the substituents $R^1$ to $R^5$ are identical or different and each denotes hydrogen or alkyl of up to 3 carbon atoms, especially hydrogen or methyl. $R^6$ and $R^7$ denote hydrogen or alkyl of up to 8 carbon atoms, such as methyl, ethyl, n-propyl, isopropyl, butyl, hexyl, heptyl and octyl.

$R^7$ may also denote alkoxyalkyl of up to 6 carbon atoms or dialkoxyalkyl of up to 8 carbon atoms, e.g., methoxymethyl and dimethoxymethyl. $R^6$ and $R^7$ may together form a methylene chain of 4 or 5 carbon atoms. R denotes haloalkyl of up to 3 carbon atoms, preferably chloroalkyl, and especially chloromethyl and dichloromethyl.

Preferred tetrahydro-1,3-oxazines are N-dichloroacetyl-4,4-dimethyltetrahydro-1,3-oxazine and N-dichloroacetyl-4,4,6-trimethyltetrahydro-1,3-oxazine.

The novel tetrahydro-1,3-oxazines of the formula II are obtained by reaction of a compound of the formula

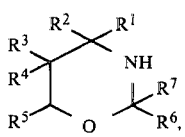

where $R^1$, $R^2$, $R^3$, $R^4$, $R^5$, $R^6$ and $R^7$ have the above meanings, with an acid chloride of the formula R-CO-Cl IV;

where R has the above meanings, in the presence of an agent which binds hydrogen chloride and in an inert solvent or diluent.

Examples of agents which bind hydrogen chloride are inorganic bases, such as alkali metal carbonates, alkali metal bicarbonates and alkali metal hydroxides, and organic bases, e.g., tertiary amines, such as trialkylamines, and especially triethylamine.

Suitable inert solvents or diluents are hydrocarbons, such as toluene, xylenes, ligroin and cyclohexane, halogenated hydrocarbons, such as dichloromethane, chloroform and carbon tetrachloride, and ethers, such as diethyl ether, diisopropyl ether, tetrahydrofuran, dioxane and anisole.

The following example illustrates the production of the new tetrahydro-1,3-oxazines. Parts by weight bear the same relationship to parts by volume as kilograms to liters.

EXAMPLE 1

At $-10°$ C. and while stirring, 23.2 parts by weight of dichloroacetyl chloride in 100 parts by volume of toluene is dripped into 23.0 parts by weight of 4,4-dimethyltetrahydro-1,3-oxazine and 20.7 parts by weight of triethylamine in 100 parts by volume of toluene. After the mixture has been stirred for 2 hours at room temperature, there are added 150 parts by volume of methylene chloride and enough water for 2 clear phases to be formed. The organic phase is separated and washed twice, each time with 50 parts by volume of water. After drying and evaporation of the solvents under reduced pressure, there is isolated 41 parts by weight of N-dichloroacetyl-4,4-dimethyltetrahydro-1,3-oxazine of melting point 105°–106° C., which melts, after recrystallization from methanol, at 106°–107° C.

| $C_8H_{13}N_2O_2Cl_2$ | | MW: 226 | |
|---|---|---|---|
| calc.: | C 42.5 | H 5.8 | N 6.19 |
| found: | C 42.6 | H 5.8 | N 6.2 |

The following compounds may be prepared analogously:

 

| No. | R | $R^1$ | $R^2$ | $R^3$ | $R^4$ | $R^5$ | $R^6$ | $R^7$ | m.p./b.p./$n_D^{25}$ |
|---|---|---|---|---|---|---|---|---|---|
| 1 | $CH_2Cl$ | $CH_3$ | $CH_3$ | H | H | H | H | H | b.p.$_{0.067\ mbar}$ 90° C. |
| 2 | $CH_2Cl$ | $CH_3$ | $CH_3$ | H | H | $CH_3$ | H | H | |
| 3 | $CHCl_2$ | $CH_3$ | $CH_3$ | H | H | H | H | H | m.p.: 108° C. |
| 4 | $CHCl_2$ | $CH_3$ | $CH_3$ | H | H | H | $CH_3$ | H | oil |
| 5 | $CHCl_2$ | $CH_3$ | $CH_3$ | H | H | H | $C_2H_5$ | H | 1.5152 |
| 6 | $CHCl_2$ | $CH_3$ | $CH_3$ | H | H | H | $n-C_3H_7$ | H | 1.5010 |
| 7 | $CHCl_2$ | $CH_3$ | $CH_3$ | H | H | H | $i-C_3H_7$ | H | |
| 8 | $CHCl_2$ | $CH_3$ | $CH_3$ | H | H | H | $CH_3$ | $CH_3$ | |
| 9 | $CHCl_2$ | $CH_3$ | $CH_3$ | H | H | H | $CH_3$ | $C_2H_5$ | |
| 10 | $CHCl_2$ | $CH_3$ | $CH_3$ | H | H | H | $CH_3$ | $CH_3OCH_2$ | |
| 11 | $CHCl_2$ | $CH_3$ | $CH_3$ | H | H | $CH_3$ | H | H | m.p.: 56° C. |
| 12 | $CHCl_2$ | $CH_3$ | $CH_3$ | H | H | $CH_3$ | $CH_3$ | H | 1.4918 |
| 13 | $CHCl_2$ | $CH_3$ | $CH_3$ | H | H | $CH_3$ | $C_2H_5$ | H | 1.4949 |
| 14 | $CHCl_2$ | $CH_3$ | $CH_3$ | H | H | $CH_3$ | $n-C_3H_7$ | H | 1.4915 |
| 15 | $CHCl_2$ | $CH_3$ | $CH_3$ | H | H | $CH_3$ | $i-C_3H_7$ | H | 1.4945 |
| 16 | $CHCl_2$ | H | H | $CH_3$ | $CH_3$ | H | H | H | m.p.: 64° C. |
| 17 | $CHCl_2$ | H | H | $CH_3$ | $CH_3$ | H | $CH_3$ | H | m.p: 80° C. |
| 18 | $CHCl_2$ | H | H | $CH_3$ | $CH_3$ | H | $C_2H_5$ | H | |
| 19 | $CHCl_2$ | H | H | $CH_3$ | $CH_3$ | H | $i-C_3H_7$ | H | m.p: 84° C. |
| 20 | $CHCl_2$ | H | H | $CH_3$ | $CH_3$ | $CH_3$ | H | H | |
| 21 | $CHCl_2$ | H | H | $CH_3$ | $CH_3$ | $CH_3$ | $CH_3$ | H | |
| 22 | $CHCl_2$ | H | H | $CH_3$ | $CH_3$ | $CH_3$ | $C_2H_5$ | H | |
| 23 | $CHCl_2$ | H | H | $CH_3$ | $CH_3$ | $CH_3$ | $i-C_3H_7$ | H | |
| 24 | $CHCl_2$ | H | H | $CH_3$ | $CH_3$ | H | $CH_3$ | $CH_3$ | |
| 25 | $CHCl_2$ | H | H | $CH_3$ | $CH_3$ | H | $CH_3$ | $CH_3OCH_2$ | |
| 26 | $CHCl_2$ | $CH_3$ | $CH_3$ | H | H | $CH_3$ | $CH-nC_4H_9$<br>\|<br>$C_2H_5$ | H | 1.4849 |
| 27 | $CHCl_2$ | $CH_3$ | $CH_3$ | H | H | $CH_3$ | $CH_3$ | $CH_3$ | |
| 28 | $CHCl_2$ | $CH_3$ | $CH_3$ | H | H | $CH_3$ | $CH_3$ | $C_2H_5$ | |
| 29 | $CHCl_2$ | $CH_3$ | $CH_3$ | H | H | $CH_3$ | H | $CH(OCH_3)_2$ | oil |
| 30 | $CHCl_2$ | $CH_3$ | $CH_3$ | H | H | $CH_3$ | $CH_3$ | $CH_3OCH_2$ | oil |
| 31 | $CHCl_2$ | $CH_3$ | $CH_3$ | H | H | $CH_3$ | $-(CH_2)_4-$ | | oil |
| 32 | $CHCl_2$ | $CH_3$ | $CH_3$ | H | H | $CH_3$ | $-(CH_2)_5-$ | | oil |
| 33 | $CCl_3$ | $CH_3$ | $CH_3$ | H | H | H | H | H | m.p.: 103° C. |
| 34 | $CCl_3$ | $CH_3$ | $CH_3$ | H | H | $CH_3$ | H | H | |
| 35 | $CH_2-CH_2Cl$ | $CH_3$ | $CH_3$ | H | H | H | H | H | |
| 36 | $CH_2-CH_2Cl$ | $CH_3$ | $CH_3$ | H | H | $CH_3$ | H | H | |

Some of the starting materials of the formula III needed the preparation of the new tetrahydro-1,3-oxazines are known from Rec. trav. chim. P.B., 78, 315, 1959 and J. Org. Chem., 38, 36, 1973. They may be prepared by conventional methods (Tetrahedron, 30, 3315, 1974; Rec. trav. chim. P.B., 78, 315, 1959) in accordance with the following equation:

weight of water is separated off over a period of 2 hours by azeotropic distillation. The reaction product is subjected to fractional distillation. After removal of the solvent there is obtained 1,372 parts by weight of 2,4,4,6-tetramethyltetrahydro-1,3-oxazine with a purity (according to gas chromatography) of 98%, equivalent to a yield of 94% of theory, based on 2-methyl-2-aminopentan-4-ol.

Boiling point (13 mbars): 53°–54° C.

$n_D^{20}$: 1.4340.

The following compounds of the formula III are prepared in the same way.

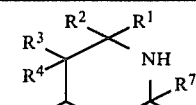

| $R^1$ | $R^2$ | $R^3$ | $R^4$ | $R^5$ | $R^6$ | $R^7$ | $n_D^{20}$ | b.p. (mbars) [°C.] |
|---|---|---|---|---|---|---|---|---|
| CH$_3$ | CH$_3$ | H | H | H | H | H | 1.4290 | b.p.$_{(153)}$ 87 |
| CH$_3$ | CH$_3$ | H | H | H | H | CH$_3$ | 1.4372 | b.p.$_{(20)}$ 42–43 |
| CH$_3$ | CH$_3$ | H | H | H | H | C$_2$H$_5$ | 1.4392 | b.p.$_{(26.6)}$ 48–49 |
| CH$_3$ | CH$_3$ | H | H | H | H | nC$_3$H$_7$ | 1.4371 | b.p.$_{(26.6)}$ 69–70 |
| CH$_3$ | CH$_3$ | H | H | H | H | iC$_3$H$_7$ | 1.4391 | b.p.$_{(26.6)}$ 68–69 |
| CH$_3$ | CH$_3$ | H | H | H | H | CH(C$_4$H$_9$)(C$_2$H$_5$) | 1.4442 | b.p.$_{(0.27)}$ 54–55 |
| CH$_3$ | CH$_3$ | H | H | CH$_3$ | H | H | 1.4394 | b.p.$_{(13.3)}$ 47–48 |
| CH$_3$ | CH$_3$ | H | H | CH$_3$ | H | CH$_3$ | 1.4340 | b.p.$_{(13.3)}$ 53–54 |
| CH$_3$ | CH$_3$ | H | H | CH$_3$ | H | C$_2$H$_5$ | 1.4345 | b.p.$_{(13.3)}$ 58–59 |
| CH$_3$ | CH$_3$ | H | H | CH$_3$ | H | nC$_3$H$_7$ | 1.4380 | b.p.$_{(0.27)}$ 41–43 |
| CH$_3$ | CH$_3$ | H | H | CH$_3$ | H | iC$_3$H$_7$ | 1.4341 | b.p.$_{(13.3)}$ 65–67 |
| CH$_3$ | CH$_3$ | H | H | CH$_3$ | H | CH(C$_4$H$_9$)(C$_2$H$_5$) | 1.4451 | b.p.$_{(0.27)}$ 54–55 |
| CH$_3$ | CH$_3$ | H | H | H | CH$_3$ | C$_2$H$_5$ | 1.4451 | b.p.$_{(20)}$ 59–60 |
| CH$_3$ | CH$_3$ | H | H | CH$_3$ | CH$_3$ | CH$_3$OCH$_2$ | 1.4415 | b.p.$_{(26.6)}$ 96 |
| CH$_3$ | CH$_3$ | H | H | H | —(CH$_2$)$_4$— | | 1.4689 | b.p.$_{(26.6)}$ 97–98 |
| CH$_3$ | CH$_3$ | H | H | CH$_3$ | —(CH$_2$)$_4$— | | 1.4651 | b.p.$_{(0.27)}$ 47–48 |
| CH$_3$ | CH$_3$ | H | H | CH$_3$ | —(CH$_2$)$_5$— | | 1.4690 | b.p.$_{(0.27)}$ 46–47 |
| H | H | CH$_3$ | CH$_3$ | H | H | H | | |
| H | H | CH$_3$ | CH$_3$ | H | CH$_3$ | H | | |
| H | H | CH$_3$ | CH$_3$ | H | i-C$_3$H$_7$ | H | | |

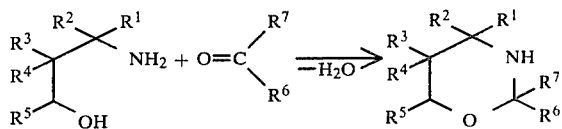

III

The following example illustrates the preparation of the starting materials. Parts by weight bear the same relationship to parts by volume as kilograms to liters.

EXAMPLE 2

1,170 parts by weight of 2-methyl-2-aminopentan-4-ol is placed in a stirred flask. With external cooling, 440 parts by weight of acetaldehyde is run in over a period of about 40 minutes at 15°–20° C. The reaction mixture is stirred for a further 15 minutes at 20° C. After the addition of 600 parts by volume of toluene, 182 parts by Herbicidal active ingredients and antagonistic compounds may be incorporated into the soil either together or separately and before or after sowing. With acetanilides, the commonest method is to apply them to the surface of the soil immediately after sowing, or in the period between sowing and emergence of the young plants. It is also possible to apply them during emergence. In each instance, the antagonistic agent may be applied simultaneously with the herbicidal active ingredient. It is also possible to apply the compounds separately—either the antagonist first and then the herbicidal active ingredient, or vice versa—provided that, if the herbicidal active ingredient is applied first, not too much time elapses before the antagonist is applied as otherwise the crop plants may be damaged. The active ingredient and antagonist may be suspended, emulsified or dissolved in a spray liquor or may be in granular form, and may be formulated together or separately. It is also feasible to treat the seed with the antagonist before sowing. The herbicidal active ingredient is then applied on its own in the usual manner.

Varying amounts of antagonistic compound are required for the same herbicidal acetanilide when it is used in different crops. The ratio of acetanilide to tetrahydro-1,3-oxazine may be varied within a wide range; it is dependent on the structure of the anilide and of the tetrahydro-1,3-oxazine, and on the crop in which they are used. Suitable ratios of herbicidal active ingredient to antagonist are from 1:2 to 1:0.05 parts by weight.

The novel herbicidal agents may contain, in addition to acetanilide and tetrahydro-1,3-oxazine, other herbicidal or growth-regulating active ingredients of different chemical structure, e.g., 2-chloro-4-ethylamino-6-isopropylamino-1,3,5-triazine, without the antagonistic effect being impaired.

The agents according to the invention, or, when applied separately, the herbicidal active ingredients and the antidote are applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the herbicidal active ingredient and/or antidote as such or dissolved in an oil or solvent may be homogenized in water by means of wetting or dispersing agents, adherents or emulsifiers. Concentrates which are suitable for dilution with water may be prepared from herbicidal active ingredient and/or antidote, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the herbicidal active ingredient and/or antidote with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of herbicidal active ingredient and antidote. Application rates of the herbicidal active ingredient are from 0.2 to 5 kg of active ingredient per hectare. The herbicidal active ingredient is applied either together with or separately from the antidote in such a manner that the ratio of herbicidal active ingredient to antagonist is from 1:2 to 1:0.05 parts by weight.

Examples of formulations are given below.

I. 40 parts by weight of a mixture of 4 parts by weight of 2-chloro-2',6'-dimethyl-N-(pyrazol-1-yl-methyl)-acetanilide and 1 part by weight of N-dichloroacetyl-4,4-dimethyltetrahydro-1,3-oxazine is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient + antidote.

II. 3 parts by weight of a mixture of 1 part by weight of 2-chloro-2',6'-dimethyl-N-(pyrazol-1-yl-methyl)-acetanilide and 1 part by weight of N-dichloroacetyl-4,4,6-trimethyltetrahydro-1,3-oxazine is intimately mixed with 97 parts by weight of particulate kaolin. A dust is obtained containing 3% by weight of active ingredient + antidote.

III. 30 parts by weight of a mixture of 1 part by weight of 2-chloro-2'-methyl-6'-ethyl-N-(1,2,4-trizaol-1-yl-methyl)-acetanilide and 2 parts by weight of N-dichloroacetyl-2-ethyl-4,4,6-trimethyltetrahydro-1,3-oxazine is intimately mixed with a mixture consisting of 92 parts by weight of powdered silica gel and 8 parts by weight of paraffin oil which has been sprayed onto the surface of this silica gel. A formulation is obtained having good adherence.

IV. 20 parts by weight of a mixture of 8 parts by weight of 2-chloro-2'-methyl-6'-ethyl-N-(pyrazol-1-yl-methyl)-acetanilide and 1 part by weight of N-dichloroacetyl-2-n-propyl-4,4,6-trimethyl-1,3-tetrahydro-1,3-oxazine is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

V. 20 parts by weight of a mixture of 10 parts by weight of 2-chloro-2',6'-dimethyl-N-(4,5-dichloroimidazol-1-yl-methyl)-acetanilide and 1 part by weight of N-dichloroacetyl-4,4-dimethyltetrahydro-1,3-oxazine is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and finely distributing it therein, an aqueous dispersion is obtained containing 0.02% by weight of active ingredient+antidote.

The influence of various representatives of the agents according to the invention (herbicidal active ingredient-+antagonist) on the growth of unwanted and crop plants compared with that of agents consisting of the same herbicidal active ingredients and an already known antagonistic compound having a chemical structure similar to that of the antagonists in the agents according to the invention is demonstrated in the following biological examples. The experiments show that tolerance of the herbicidal acetanilides is improved, without the herbicidal action being impaired, when they are combined with the new tetrahydro-1,3-oxazines.

The series of experiments were carried out in the greenhouse and in the open.

I. Greenhouse experiments

Plastic boxes 51 cm long, 32 cm wide and 6 cm deep were filled with loamy sand (pH:6) containing about 1.5% humus. Indian corn (Zea mays) or wheat (Triticum aestivum) were sown shallow, in rows, in this substrate. Echinochloa crus-galli and Alopecurus were scattered random as unwanted plants. The non-sterilized soil also additionally contained viable weed seeds which contributed to the weed population. A field with crop plants growing in it and infested with weeds was thus simulated.

The active ingredients and antagonists were applied separately and in the mixtures given below. They were emulsified or suspended in water as vehicle and the liquor sprayed through finely distributing nozzles onto the soil surface, either immediately after sowing or prior to emergence of the test plants. In some cases, the agents were also incorporated into the soil before the crop plants were sown. After sowing and treatment the boxes were sprinkler-irrigated and covered with transparent plastic hoods until the plants emerged. These measures ensured that the plants germinated and took root uniformly. The boxes were set up in the greenhouse at from 18° to 30° C.

These greenhouse experiments were monitored until 3 to 5 Indian corn leaves had developed. No more damage due to the herbicidal agents was to be expected after this stage, a fact which was confirmed by the experiments in the open. The scale for assessing the action of the agents was 0 to 100, 0 denoting normal emergence and development of the plants, with reference to the untreated control, and 100 denoting non-germination or withering of the plants. It should be borne in mind here that, for instance in Indian corn, odd crippled or retarded plants may occur even under completely normal conditions and without any chemical treatment.

II. Experiments in the open

These experiments were run on small plots in loamy sand and loam (pH: 5 to 6) with a humus content of 1 to 1.5%. Pre-emergence treatment took place either immediately after the crop plants had been sown, or at the latest 3 days later. The weed flora was made up of various species and was naturally occurring. However, only the dominating representatives have been included in the tables. Active ingredients and antagonists, and combinations thereof, were emulsified or suspended in water as vehicle and applied by means of a motor-driven plot spray mounted on a tractor. Where no rain fell, the plots were sprinkled to ensure normal emergence of the crop plants and weeds. All the experiments were run for several months, thus enabling the development of the crop plant up to seed formation to be observed. Assessment of the action of the agents was also made on the 0 to 100 scale.

Results

As a result of the shallow sowing of the crop plants and the more favorable conditions for herbicidal activity, the damage caused by the herbicidal active ingredients in the greenhouse was much greater than in the open. The test conditions for the antagonistic compounds were therefore severer in the greenhouse than in the open.

Where the new antagonistic tetrahydro-1,3-oxazines are applied on their own, they have a scarcely perceptible effect, if at all, on the germination and growth of the unwanted and crop plants. This is also apparent at application rates substantially higher than those required for antagonistic effects.

However, the new compounds reduce the phytotoxicity of the herbicidal acetanilides of the formula I to crop plants such as Indian corn and cereals to a considerable extent and in some cases eliminate it completely. It was found that in the case of herbicidal compounds which are less aggressive to crop plants it is sufficient to add smaller amounts of antagonistic compounds or antagonistic compounds having a lesser antagonistic action.

TABLE 1

List of plant names

| Botanical name | Abbreviation in tables | Common name |
|---|---|---|
| *Alopecurus myosuroides* | | slender foxtail |
| *Chenopodium album* | | lambsquarters |
| *Echinochloa crus galli* | Echinochloa c.g. | barnyardgrass |
| Galinsoga spp. | | gallant soldier |
| Hordeum vulgare | | barley |
| Matricaria Anthemis spp. | | chamomile |
| *Triticum aestivum* | | wheat |
| *Zea mays* | | Indian corn |

TABLE 2

List of the herbicidal acetanilides used in the biological examples

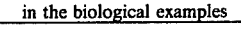

| Designation | A | R | $R^1$ | $R^2$ | m.p. [°C.] |
|---|---|---|---|---|---|
| A | -N(pyrazol-1-yl) | $CH_3$ | $CH_3$ | H | 81 |
| B | -N(pyrazol-1-yl) | $C_2H_5$ | $CH_3$ | H | 56 |
| C | -N(4-methylpyrazol-1-yl) | $CH_3$ | $CH_3$ | H | 102 |
| D | -N(4-methoxypyrazol-1-yl) | $C_2H_5$ | $CH_3$ | H | 94 |
| E | -N(3,4-dimethylpyrazol-1-yl) | $C_2H_5$ | $CH_3$ | H | oil |
| F | -N(3,5-dimethylpyrazol-1-yl) | $CH_3$ | $CH_3$ | H | 126 |
| G | -N(1,2,4-triazol-1-yl) | $CH_3$ | $CH_3$ | H | 120 |
| H | -N(4-chloropyrazol-1-yl) | $CH_3$ | $CH_3$ | H | 104 |
| I | -N(pyrazol-1-yl) | $CH_3$ | $CH_3$ | $CH_3$ | 92 |

TABLE 3

List of the antagonistic tetrahydro-1,3-oxazines used in the biological examples

| No. | $R^5$ | $R^6$ |
|---|---|---|
| 3 | H | H |
| 11 | $CH_3$ | H |
| 12 | $CH_3$ | $CH_3$ |
| 13 | $CH_3$ | $C_2H_5$ |
| 14 | $CH_3$ | $n-C_3H_7$ |
| 15 | $CH_3$ | $i-C_3H_7$ |
| 26 | $CH_3$ | $-CH(C_2H_5)-n-C_4H_9$ |

TABLE 3-continued

List of the antagonistic tetrahydro-1,3-oxazines used in the biological examples

| No. | $R^5$ | $R^6$ |
|---|---|---|
| V (prior art) | morpholino-$N-CO-CHCl_2$ | |

TABLE 4

Reduction in damage to Indian corn by 2-chloro-2',6'-dimethyl-N-(pyrazol-1-yl-methyl)-acetanilide when antagonistic tetrahydro-1,3-oxazines are added; preemergence treatment in the greenhouse

| Herbicidal active ingredient | Antagonistic compound | Appln. rate [kg/ha] | Crop plant Zea mays | Alopecurus myosoroides | Echinochloa c.g. |
|---|---|---|---|---|---|
| A | — | 1.0 | 57 | 100 | 100 |
|   |   | 2.0 | 73 | 100 | 100 |
| A | 3 | 1 + 0.125 | 8 | 99 | 99 |
|   |   | 1 + 1.0 | 5 | 100 | 100 |
|   |   | 1 + 2.0 | 5 | 100 | 100 |
|   |   | 2 + 0.25 | 15 | 100 | 100 |
|   |   | 2 + 0.5 | 10 | 100 | 100 |
| A | 11 | 1 + 0.125 | 0 | 98 | 98 |
|   |   | 1 + 0.25 | 0 | 100 | 100 |
|   |   | 1 + 2.0 | 5 | 100 | 100 |
|   |   | 2 + 0.5 | 10 | 100 | 100 |
|   |   | 2 + 2.0 | 10 | 100 | 100 |
| A | 12 | 1 + 0.25 | 15 | 100 | 100 |
|   |   | 1 + 2.0 | 15 | 100 | 100 |
| A | 13 | 1 + 0.25 | 25 | 100 | 100 |
|   |   | 1 + 2.0 | 25 | 100 | 100 |
| A | 14 | 1 + 2 | 25 | 100 | 100 |
| A | 15 | 1 + 0.25 | 20 | 100 | 100 |
| A | 26 | 1 + 0.25 | 20 | 100 | 100 |
| — | 3 | 4.0 | 2.5 | 0 | 0 |
| — | 11 | 4.0 | 0 | 0 | 0 |
| — | 12 | 4.0 | 0 | 0 | 0 |
| — | 13 | 4.0 | 0 | 0 | 0 |
| — | 14 | 4.0 | 0 | 0 | 0 |
| — | 15 | 4.0 | 0 | 0 | 0 |
| — | 26 | 4.0 | 0 | 0 | 0 |

0 = normal emergence, no damage
100 = non-emergence, or plants withered

TABLE 5

Improvement in the tolerance of herbicidal acetanilides by Indian corn due to antagonistic tetrahydro-1,3-oxazines; preemergence treatment in the greenhouse

| Herbicidal active ingredient | Antagonistic compound | Appln. rate [kg/ha] | Crop plant Zea mays | Unwanted plant Echinochloa c.g. |
|---|---|---|---|---|
| A | — | 1.0 | 88 | 100 |
|   |   | 2.0 | 90 | 100 |
| — | 3 | 4.0 | 10 | 0 |
| A | 3 | 1.0 + 0.125 | 10 | 100 |
|   |   | 1.0 + 0.5 | 0 | 100 |
|   |   | 1.0 + 2.0 | 5 | 100 |
| B | — | 1.0 | 70 | 100 |
|   |   | 2.0 | 88 | 100 |
| B | 3 | 1.0 + 0.25 | 0 | 100 |
|   |   | 2.0 + 0.5 | 5 | 100 |
|   |   | 2.0 + 2.0 | 5 | 100 |
| C | — | 1.0 | 30 | 100 |
|   |   | 2.0 | 70 | 100 |

TABLE 5-continued

Improvement in the tolerance of herbicidal acetanilides by Indian corn due to antagonistic tetrahydro-1,3-oxazines; preemergence treatment in the greenhouse

| Herbicidal active ingredient | Antagonistic compound | Appln. rate [kg/ha] | Crop plant Zea mays | Unwanted plant Echinochloa c.g. |
|---|---|---|---|---|
| C | 3 | 1.0 + 0.25 | 0 | 100 |
|   |   | 1.0 + 1.0 | 0 | 100 |
|   |   | 2.0 + 0.25 | 0 | 100 |
|   |   | 2.0 + 2.0 | 5 | 100 |
| D | — | 1.0 | 10 | 100 |
|   |   | 2.0 | 65 | 100 |
| D | 3 | 1.0 + 0.25 | 0 | 100 |
|   |   | 1 + 1 | 0 | 100 |
|   |   | 2.0 + 0.5 | 5 | 100 |
|   |   | 2.0 + 2.0 | 0 | 100 |
| E | — | 1.0 | 70 | 100 |
|   |   | 2.0 | 80 | 100 |
| E | 3 | 1.0 + 0.25 | 0 | 100 |
|   |   | 2.0 + 0.5 | 0 | 100 |
| F | — | 1.0 | 70 | 100 |
|   |   | 2.0 | 85 | 100 |
| F | 3 | 1.0 + 1.0 | 10 | 100 |
|   |   | 1.0 + 0.25 | 20 | 100 |
|   |   | 2.0 + 2.0 | 10 | 100 |
| G | — | 1.0 | 30 | 99 |
|   |   | 2.0 | 62 | 100 |
| G | 3 | 1.0 + 0.125 | 5 | 98 |
|   |   | 1.0 + 1.0 | 5 | 98 |
|   |   | 2.0 + 0.5 | 10 | 98 |
| H | — | 2.0 | 8 | 96 |
| H | 3 | 2.0 + 0.5 | 5 | 95 |
| I | — | 1.0 | 75 | 98 |
| I | 3 | 1.0 + 1.0 | 0 | 96 |
|   |   | 1.0 + 0.125 | 5 | 95 |

0 = normal emergence, no damage
100 = non-emergence, or plant destroyed

TABLE 6

Improvement in the tolerance of 2-chloro-2',6'-dimethyl-N-(pyrazol-1-yl-methyl)-acetanilide by Indian corn due to admixture of antagonistically active N-dichloroacetyl-4,4-dimethyltetrahydro-1,3 oxazine

| Herbicidal active ingredient | Antagonistic compound | Appln. rate [kg/ha] | Crop plant Zea mays | Chenopodium album | Matricarial Anthemis spp. | Galinsoga spp. |
|---|---|---|---|---|---|---|
| A | — | 1.0 | 4 | 95 | 100 | 98 |
|   |   | 2.0 | 15 | 100 | 100 | 100 |
|   |   | 3.0 | 14 | 100 | 100 | — |
| A | 3 | 1 + 0.125 | 0 | — | — | — |
|   |   | 1 + 0.5 | 2 | 98 | 100 | 100 |
|   |   | 2 + 0.25 | 2,5 | — | 100 | — |
|   |   | 2 + 1.0 | 5 | 100 | 100 | 100 |
|   |   | 3 + 1.0 | 5 | 100 | 100 | — |

0 = normal emergence, no damage
100 = non-emergence, or plants destroyed

TABLE 7

Increase in tolerance of herbicidal acetanilides by cereals due to addition of N-dichloroacetyl-4,4-dimethyltetrahydro-1,3-oxazine; preemergence treatment in the greenhouse

| Herbicidal active ingredient | Antagonistic compound | Appln. rate [kg/ha] | Hordeum vulgare | Titicum aestivum | Alopecurus myosuroides |
|---|---|---|---|---|---|
| H | — | 1.0 | 28 | 22 | 93 |
|   |   | 2.0 | 60 | 45 | 98 |
| H | 3 | 2.0 + 0.5 | 20 | 2 | 94 |
|   |   | 1.0 + 1.0 | 2 | 5 | 82 |
|   |   | 1.0 + 0.125 | 15 | 5 | 92 |
|   |   | 1.0 + 2.0 | 5 | 5 | 95 |
| D | — | 1.0 | 35 | 35 | 94 |
| D | 3 | 1.0 + 0.5 | 32 | 15 | 98 |
|   |   | 1.0 + 2.0 | 5 | 5 | 94 |

TABLE 8

Comparison of the antagonistic action of a tetrahydro-1,3-oxazine according to the invention with that of a prior art antagonist; preemergence treatment in the greenhouse

| Herbicidal active ingredient | Antagonistic compound | Appln. rate [kg/ha] | Crop plant Zea mays | Unwanted plant Echinochloa c.g. |
|---|---|---|---|---|
| A | — | 1.0 | 74 | 99 |
|   |   | 2.0 | 82 | — |
|   |   | 3.0 | 84 | — |
| — | 3 | 4.0 | 1 | 0 |
| — | V (prior art) | 4.0 | 1 | 2 |
| A | 3 | 1.0 + 0.125 | 18 | 99 |
|   |   | 2.0 + 0.5 | 26 | — |
|   |   | 3.0 + 0.5 | 42 | — |
| A | V (prior art) | 1.0 + 0.125 | 42 | 99 |
|   |   | 2.0 + 0.5 | 48 | — |
|   |   | 3.0 + 0.5 | 70 | — |

0 = normal emergence, no damage
100 = non-emergence, or plants destroyed

We claim:

1. A tetrahydro-1,3-oxazine of the formula

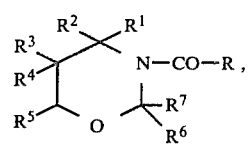

where R denotes linear or branched haloalkyl of up to 3 carbon atoms, $R^1$, $R^2$, $R^3$, $R^4$ and $R^5$ are identical or different and each denotes hydrogen or linear or branched alkyl of up to 3 carbon atoms, $R^6$ denotes hydrogen, or $R^7$ denotes hydrogen.

2. N-dichloroacetyl-4,4-dimethyltetrahydro-1,3-oxazine.

3. N-dichloroacetyl-4,4,6-trimethyltetrahydro-1,3-oxazine.

4. A herbicidal agent comprising, as herbicidal active ingredient, at least one substituted acetanilide of the formula

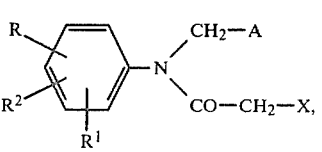

where R denotes hydrogen, linear or branched alkyl or alkoxy of up to 5 carbon atoms, $R^1$ denotes hydrogen, halogen, or linear or branched alkyl or alkoxy of up to 5 carbon atoms, $R^2$ denotes hydrogen, halogen, or linear or branched alkyl or alkoxy of up to 5 carbon atoms, R together with $R^2$ denotes an alkylene chain of up to 6 carbon atoms which is linked in the o-position and may be substituted by linear or branched alkyl of up to 4 carbon atoms, X denotes chlorine or bromine, and A denotes azole which is attached via a ring nitrogen atom and may be mono- or polysubstituted by halogen, phenyl, alkyl, alkoxy, alkylthio or perfluoroalkyl, each of up to 4 carbon atoms, cyano, carboxy, carbalkoxy of up to 4 carbon atoms in the alkoxy, or alkanoyl of up to 4 carbon atoms, or A denotes salts of azoles containing 2 or 3 nitrogen atoms, and, as antagonistic agent, at least one tetrahydro-1,3-oxazine of the formula

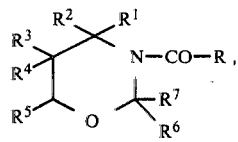
II where R denotes linear or branched haloalkyl of up to 3 carbon atoms, $R^1$, $R^2$, $R^3$, $R^4$ and $R^5$ are identical or different and each denotes hydrogen or linear or branched alkyl of up to 3 carbon atoms, $R^6$ denotes hydrogen, or $R^7$ denotes hydrogen.

5. A herbicidal agent as claimed in claim 4, comprising 2-chloro-2',6'-dimethyl-N-(pyrazol-1-yl-methyl)-acetanilide as herbicidal active ingredient and N-dichloroacetyl-4,4-dimethyltetrahydro-1,3-oxazine as antagonistic agent.

6. A herbicidal agent as claimed in claim 4, comprising 2-chloro-2',6'-dimethyl-N-(pyrazol-1-yl-methyl)-acetanilide as herbicidal active ingredient and N-dichloroacetyl-4,4,6-trimethyltetrahydro-1,3-oxazine as antagonistic agent.

7. A herbicidal agent as claimed in claim 4, wherein the ratio of acetanilide to tetrahydro-1,3-oxazine, applied separately or together, is from 1:2 to 1:0.05 parts by weight.

8. A process for the selective control of unwanted plants, wherein a substituted acetanilide of the formula I and a tetrahydro-1,3-oxazine of the formula II are applied, either simultaneously or one after the other in any order, before, during or after sowing of the crop plants or before or during emergence of the crop plants.

9. A process for the selective control of unwanted plants, wherein the crop plant seed is treated with one or several tetrahydro-1,3-oxazines of the formula II.

10. A process as claimed in claims 8 and 9, wherein the crop plant is Indian corn or a cereal.

* * * * *